United States Patent [19]

Wiegerinck

[11] Patent Number: 4,723,940
[45] Date of Patent: Feb. 9, 1988

[54] METHOD AND DEVICE TO PERFORATE, IN PARTICULAR TO PUNCTURE A MEMBRANOUS MEMBER WHILE UTILIZING VACUUM FIXATION

[75] Inventor: Martinus A. H. M. Wiegerinck, Eindhoven, Netherlands

[73] Assignee: Akuaba B.V., Eindhoven, Netherlands

[21] Appl. No.: 709,320

[22] PCT Filed: Jun. 15, 1984

[86] PCT No.: PCT/NL84/00020
  § 371 Date: Feb. 15, 1985
  § 102(e) Date: Feb. 15, 1985

[87] PCT Pub. No.: WO85/00009
  PCT Pub. Date: Jan. 3, 1985

[30] Foreign Application Priority Data

Jun. 15, 1983 [DE] Fed. Rep. of Germany ....... 3321621

[51] Int. Cl.[4] .............................................. A61M 5/00
[52] U.S. Cl. ..................................................... 604/115
[58] Field of Search ........ 604/115; 128/749, 751–754, 128/757–758, 643

[56] References Cited

U.S. PATENT DOCUMENTS

| | | | |
|---|---|---|---|
| 1,934,046 | 11/1933 | Demarchi | 604/115 |
| 2,945,496 | 7/1960 | Fosdal | 604/115 |
| 4,177,814 | 12/1979 | Knepshield et al. | |
| 4,222,380 | 9/1980 | Terayama | 604/115 |
| 4,299,219 | 11/1981 | Norris, Jr. | 604/115 |
| 4,393,870 | 2/1981 | Wagner | 604/115 |

FOREIGN PATENT DOCUMENTS 0936924 6/1982 U.S.S.R. .............................. 604/115

*Primary Examiner*—Kyle L. Howell
*Assistant Examiner*—Angela D. Sykes
*Attorney, Agent, or Firm*—Fleit, Jacobson, Cohn & Price

[57] ABSTRACT

The present invention includes a method and apparatus for transferring a specific amount of solid, gaseous or fluid medium to or from a space through the wall of a flexible, membranous member which encloses the space. A suction force is applied on part of the membranous member resulting in a locally increasing yet allowable deformation by tensioning of the membranous member. The pretensioned membranous member is then perforated by a needle-shaped instrument. This vacuum fixation is obtained by using a cup-shaped member of which a circumferential edge is first brought into a sealing contact with the membranous member before the suction force is applied. A hollow guiding tube guides a catheter-needle unit. One end of the hollow guiding tube is provided with the cup-shaped member which is connected to the vacuum outlet, preferably a disconnectable vacuum outlet.

4 Claims, 7 Drawing Figures

METHOD AND DEVICE TO PERFORATE, IN PARTICULAR TO PUNCTURE A MEMBRANOUS MEMBER WHILE UTILIZING VACUUM FIXATION

BACKGROUND OF THE INVENTION

The invention relates to the perforation, in particular the puncture of a membranous member while utilizing vacuum fixation. Such a method may be applicable to veterinarian techniques or techniques which involve the determination of the exact composition of substances which are located on either side of an elastic, possibly permeable membrane e.g. by taking a sample. In medicine, when the general method of vacuum fixation is used, the protection of the invention may extend to the device which causes the vacuum fixation of a tissue subjected thereto before it is perforated or punctured respectively.

The necessity to take samples from specimen e.g. which are surrounded by one or more elastic foils is well-known in laboratory research. In order to prevent possible contamination while sampling, e.g. by bacteria, it may be desirable to take a sample very cautiously via flexible membrane walls which act like a sterile sluice as it were. A similar sampling occurs also during the cultivation of specific organisms, whether or not in connection with multiplication or for research into syndromes or impacts of other materials. In all these cases the intended vacuum fixation is applicable.

The object of the invention is to perforate the membranous member at the eact location, while utilizing vacuum fixation, in particular to puncture without causing of undesirable damages or undesirable contamination inside the space which is enclosed by the membranous member.

The method according to the invention is based on the transfer of a specific amount of solid, gaseous or fluid medium to or from a space through an enclosing, flexible membranous member which is enclosed by said membrane, thereby utilizing a suction force that is applied on part of the membrane surface, resulting in a locally increasing yet allowable deformation by tensioning of said surface, after which the locally pre-tensioned membrane is punctured by means of an instrument, in particular a needle-shaped instrument, the required amount of medium is transferred with respect to said space through a supply or drain tube fixed in or at said instrument, and the instrument is then withdrawn from the membrane surface puncture, the local suction force then being released and whereafter the membrane elastically returns to its original position.

Vacuum fixation while utilizing puncture technique includes several possibilities. The invention can be used to perform a Douglas puncture e.g. to obtain peritoneal fluid. When a Douglas puncture is performed, it can happen that the tissue of the back part of the vagina dome and the Douglas peritoneum, which is located behind it, give way in the direction of the abdominal cavity. In that case, danger arises that other tissues, e.g. the intestines, will be punctured inadvertently and unintendedly, which can give rise to infection. Due to these dangers, one is obliged to operate through surgery in order to obtain peritoneal fluid, practically exclusively by means of laparoscopy.

SUMMARY OF THE INVENTION

According to the invention a device is provided, which solves among others the problem mentioned above while utilizing vacuum fixation, because the complications which can occur during a Douglas puncture are avoided. In addition to this, the procedure is considerably less painful and the chances of success in obtaining peritoneal fluid are notably increased.

There are other medical applications in which the possibility to control punctures is useful and can be accomplished by using thinner needle systems, such as the application of the echo-transducer, using vacuum fixation in order to visualize structures, spaces or organs that are to be punctured. One can touch a follicle of an ovary at sight by means of a vaginal transducer and suck in ova in order to fertilize in vitro, to puncture the ovary for research of virulent cells, to visualize the peritoneal fluid present, or to confirm or deny deformations of the intestines in the Douglas cavity. It can also be applied on pleura, abdominal, kidney and liver punctures, whether or not in combination with an echo-transducer. Also, during childbirth, the fetal pericranium can be focused by means of a small ring-shaped sucker-cup to obtain a blood sample, needed for analysis of the fetal oxygenation. In short, there are multiple and varied forms of applications, another example is drilling.

As far as the method is applied for obtaining sample material from a space which usually is accessible only via a relatively narrow entrance way, the increasing deformation by tensioning at the membrane surface can be obtained advantageously by using a cup-shaped member of which the circumferential edge is first brought into sealing contact with the membrane surface before suction force is applied, causing the sucked membrane surface to be tensioned against the inner wall of the cup-shaped member after which the puncture of the membrane takes place in the bottom portion of this member.

The methods mentioned above using vacuum fixation have in common with the medical method that the device designed for applying the identicated method is provided with a hollow guiding tube to guide an instrument known per se, such as a catheter-needle unit and one end of this hollow guiding tube is provided with a cup-shaped member which is connected to a vacuum outlet, preferably a disconnectable vacuum outlet.

Since the invention was first applied medically, the instrument causing the vacuum fixation is an important feature of the invention. Other constructions of the instrument are explained by the sub-claims.

BRIEF DESCRIPTION OF THE DRAWINGS

Hereinafter, the invention will be illustrated by means of a drawing of a device used for application of the described method.

DESCRIPTION OF THE PREFERRED EMBODIMENTS

Figure 1:
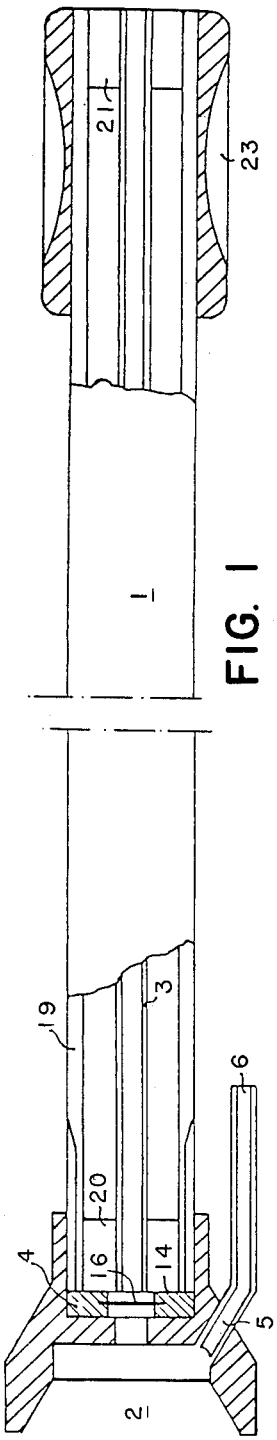
FIG. 1 shows a side view and part of a cross-section of an instrument which locally marks the pre-elected perforation spot by means of vacuum fixation.

In the drawings, the device 1 performing the vacuum fixation consists of a cup-shaped member 2 which is fixed at the end of a hollow guiding tube 3 while it is simultaneously clamping a membrane plate 4. The inner part of the cup-shaped member 2 is provided with a connection 5 to a vacuum tube 6 in which a stopvalve member (not shown) can be applied. The ring-shaped circumferential edge 7 used for vacuum fixation is brought into contact with a membranous member 8, after which the connection with the vacuum tube 6 is opened causing the membranous member 8 to be sucked in only partly or completely against the inner wall of the cup-shaped member 2, depending on the amout of underpressure. The inner shape of the cup-shaped member 2, its depth and also the circumferential size of the ring-shaped edge 7 determine the desirable or allowable deformation by tensioning of the membrane surface. Thus it is not absolutely necessary to suck in the membrane surface completely; the applied underpressure also determines how much deformation by tensioning is desirable before a perforation of the membranous member 8 takes place, in order to transfer an amount of solid, gaseous and/or fluid medium between this member 8 and the device 1.

Figure 2:
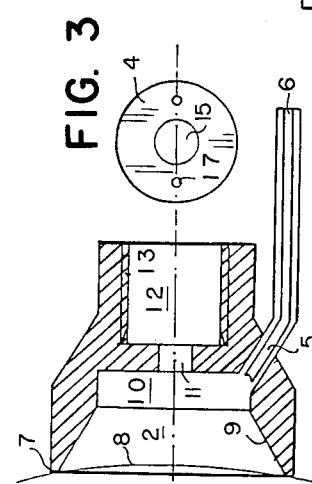
FIG. 2 shows a cross-section of the cup-shaped member including its vacuum connecting tube.
Figure 3:
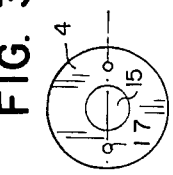
FIG. 3 shows a front view of an interchangeable membrane.
Figure 4:
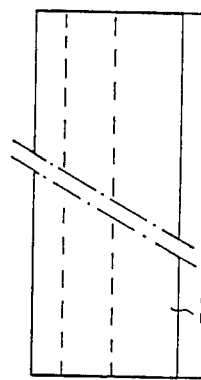
FIG. 4 shows a cross-section of the hollow guiding tube to guide the catheter-needle unit.

In the drawing, the cup-shaped member 2 has a conical wall 9 starting from the circumferential edge 7 declining inwards, which changes into a cylindrical bottom portion 10 with a central opening 11. More to the right in FIG. 2, this opening 11 is connected to a second cylindrical part 12 which is threaded internally at 13. A membrane plate 4 consits of a ring-shaped disc 14 having a central opening 15 which is slightly wider than opening 11 in the cup-shaped member 2. A sealing membrane 16 is located in the disc 14, made of latex for medical use.

After screwing in the membrane plate 4 by means of the recesses 17, the hollow guiding tube 3, which is also threaded at 18 at its left end (FIGS. 1, 2), is screwed into the cylindrical opening 13. Even though in this embodiment the membrane disc 14 is threaded at its circumference, it can also be unthreaded in which case the sealing membrane disc 14 is kept in place by screwing the end of the hollow guiding tube 3 against the membrane disc. The hollow guiding tube 3 consists of a tubular skirt 19 which, at both ends, surrounds a distance piece 20, 21 resp., which in its turn surrounds a central tub-shaped channel 22 extending over the full length of the hollow guiding tube 3. At the end of the hollow guiding tube which extends in the opposite direction of the cup-shaped member 2, a hand grip 23 is located at the outer circumference, facilitating directing it to determine the location of vacuum fixation.

Figure 6:
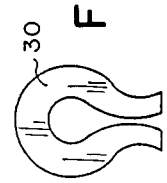
FIG. 6 shows a side view of part of a disposable depth regulator.
Figure 7:
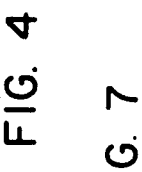
FIG. 7 shows a front view of the depth regulator in FIG. 6.
Figure 5:
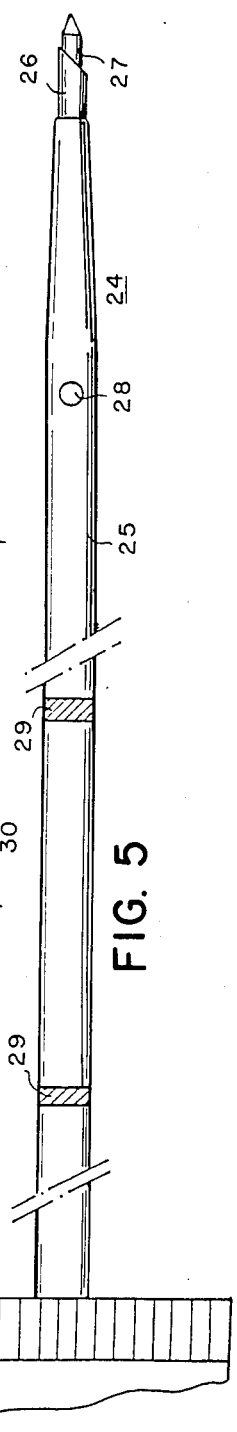
FIG. 5 shows at a larger scale a side view of a so-called depth regulator used for the device according to the invention.

In FIG. 5, a catheter-needle unit is schematically shown, consisting of a catheter 25 which envelops a hollow needle 26, provided with a rebounding inner needle 27 and a sideway opening 28 is located in the catheter. To the left in FIG. 5, the housing 31 for the catheter-needle unit is partly visible. The construction for the rebounding inner needle 26 is not specified in greater detail, since there are several manners to move the inner needle 27 relative to the hollow needle 26 with respect to performing the perforation, followed by the puncture. Two mark signs 29 are indicated on the catheter 25 and in FIG. 6 and 7 a depth regulator 30 is shown which can be longitudinally put over the catheter 25 at the location of the mark signs in order to control the required penetration. The catheter-needle unit is of such a dimension that its outer diameter is less than the inner diameter of the hollow tube-shaped channel 22. If the catheter-needle unit 24 is led into the tube-shaped channel 22 and if in FIG. 1, it is pushed to the left until the rebounding inner needle 26 rests against the membrane 16, the vacuum fixation can be performed. The membranous member 8 is then located in the immediate proximity of the central opening 11 in the cup-shaped member 2. In this position, the membrane can be perforated by means of the rebounding needle tip 27 followed by the puncture during which the inner needle 27 is withdrawn.

The method described above to perform vacuum fixation allows a precise control of location to perform certain adaptations. A medical puncture was described, but it is clear that the invention is not restricted to that. In the areas of medicine, veterinarian medicine and technique, several applications are possible which result in advantages due to the invention which need no further description. Therefore the terms used above like 'perforation' and 'puncture' must be understood in the widest sense.

I claim:

1. A method for transferring a specific amount of solid, gaseous or fluid medium to or from a space, said method comprising:
    enclosing the space between a membranous member and a sealing membrane,
    applying a suction force to the space, resulting in a deformation by tensioning of said membranous member,
    puncturing the sealing membrane and tensioned part of said membranous member by an instrument,
    transferring the specific amount of medium to said space through a tube fixed to said instrument,
    withdrawing the instrument from the puncture of the tensioned part of said membranous member, and
    releasing the suction force from said membranous member whereafter said membranous member elastically returns to its original position.

2. The method according to claim 1, wherein the deformation by tensioning of said membranous member is obtained by using a cup-shaped member having a circumferential edge first brought into a sealing contact with said membranous member before the suction force is applied, causing said membranous member to be tensioned against said circumferential edge afater which the puncture of said membranous member takes place.

3. A device for transferring a specific amount of solid, gaseous or fluid medium, said device comprising:
    a cup-shaped member having a circumferential edge adapted to be brought into sealing contact with a membranous member,
    vacuum means connected to said cup-shaped member,
    guiding tube means mounted at one end on said cup-shaped member,
    a membrane plate having a sealing membrane interposed between said cup-shaped member and said guiding tube means, said sealing membrane dividing fluid flow communication between an inlet to said cup-shaped member and said guiding tube means to define an enclosed space located between the membranous member, said cup-shaped member and said sealing membrane, said vacuum means evacuating air from air from said enclosed space to thereby tension the membranous member against said circumferential edge and providing a vacuum within said enclosed space so that when an instrument is guided through said guiding tube means to puncture said sealing membrane, travel through said inlet into said enclosed space and puncture said membranous member under tension, the specific amount of medium is transferred within a vacuum environment.

4. The method according to claim 3, wherein grip means is mounted at the other end of said guide means.

* * * * *